United States Patent
Mabilon et al.

(10) Patent No.: US 7,700,514 B2
(45) Date of Patent: Apr. 20, 2010

(54) PLATINUM-BASED, BIMETALLIC CATALYST, AND A SECOND GROUP VIII METAL USED FOR THE OPENING OF CYCLIC COMPOUNDS

(75) Inventors: Gil Mabilon, Lyons (FR); Patrice Marecot, Saint Georges les Baillargeaux (FR); Denis Uzio, Belleville (FR); Catherine Especel, Buxerolles (FR); Florence Epron, Neuville de Poitou (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 52 days.

(21) Appl. No.: 11/979,637

(22) Filed: Nov. 6, 2007

(65) Prior Publication Data
US 2008/0207437 A1 Aug. 28, 2008

(30) Foreign Application Priority Data
Nov. 7, 2006 (FR) .................. 06 09766

(51) Int. Cl.
*B01J 27/06* (2006.01)
*B01J 27/13* (2006.01)
*B01J 23/42* (2006.01)
*C07C 5/00* (2006.01)

(52) U.S. Cl. ............ 502/224; 502/230; 502/231; 502/325; 502/332; 502/334; 502/339; 585/700; 585/721; 585/722

(58) Field of Classification Search ............ 502/224, 502/230, 231, 325, 332, 334, 339
See application file for complete search history.

(56) References Cited

U.S. PATENT DOCUMENTS 3,617,511 A * 11/1971 Jenkins et al. .......... 208/112
5,763,731 A * 6/1998 McVicker et al. ........ 585/737
6,235,962 B1 * 5/2001 Zeuthen .................. 585/700
2006/0281957 A1 * 12/2006 Galperin et al. .......... 585/353

FOREIGN PATENT DOCUMENTS

EP 0 875 288 A1 11/1998
GB 2 211 756 A 7/1989

OTHER PUBLICATIONS

F. Garin, et al.; "Possible surface intermediates in alkane reactions on metallic catalyst"; Accounts of Chemical Research; 1989; pp. 100-106; vol. 22; USACS; Washington, D.C.

M.J. Dees, et al.; "Effect of platinum modification by alloying and sulfur on the hydrogenolysis and aromatization of methylcyclopentane"; Applied Catalysis; Sep. 1990; pp. 279-295; vol. 64, No. 1-2.

* cited by examiner

*Primary Examiner*—Elizabeth D Wood
(74) *Attorney, Agent, or Firm*—Millen, White, Zelano & Branigan, P.C.

(57) ABSTRACT

A catalyst comprising at least one porous support, at least some platinum, and at least a second group VIII metal which is different from platinum and iridium, said catalyst having been prepared in accordance with a process comprising a) impregnation of the support with at least one solution containing a platinum precursor, b) activation in a neutral or oxidizing atmosphere, at a temperature of between 120 and 800° C., c) activation in a reducing medium, at a temperature of between 0 and 800° C., d1) impregnation with an aqueous solution and d2) treatment with at least one hydrogen donor compound, at a temperature of less than 200° C., e) the impregnation of the support, which has already been impregnated with the platinum, with at least one solution containing a precursor of said second group VIII metal, and f) activation in a neutral, reducing, or oxidizing atmosphere, at a temperature of between 100 and 800° C.

22 Claims, No Drawings

PLATINUM-BASED, BIMETALLIC CATALYST, AND A SECOND GROUP VIII METAL USED FOR THE OPENING OF CYCLIC COMPOUNDS

DOMAIN OF INVENTION

The present invention relates to the domain of catalysts which are used in processes for the selective opening of naphthenic compounds with a view to improving the quality of petrols. To be more exact, the catalyst is a metallic catalyst intended for the selective opening of methylcyclopentane and/or methylcyclohexane.

PRIOR ART

In view of the ever stricter legislation governing environmental protection, cleaner and cleaner gasolines are having to be produced. To be specific, the gasolines which are used nowadays for car fuel must have a low content of aromatic compounds and a high content of paraffins, particularly branched paraffins with a high octane index. The production of such petrols requires complete hydrogenation of the aromatic compounds into naphthenic compounds, followed by the selective opening of said naphthenic compounds into paraffins. The selective opening reaction of naphthenic compounds into paraffins has already been described in the prior art. In particular, U.S. Pat. No. 5,763,731 teaches of the use of a catalyst containing iridium, ruthenium and/or rhodium for opening naphthenic rings, particularly rings with 6 carbon atoms containing at least one substituent having at least 3 carbon atoms. U.S. Pat. No. 5,763,731 teaches that the best catalytic results in terms of conversion and selective opening of the ring into the desired products are obtained in the presence of an iridium-based catalyst. The major drawback of iridium-based catalysts is the very low quantity of that metal in the natural state. This lack of natural availability is not compatible with large tonnage manufacture of these iridium-based catalysts for use on an industrial scale in equipment for the opening of naphthenic rings. The present invention also proposes the provision of a metallic catalyst for the purpose of carrying out a process for opening naphthenic rings, which reveals catalytic performances resembling those obtained with an iridium-based catalyst as an alternative to known prior art catalysts.

DESCRIPTION OF INVENTION

The present invention is concerned with a catalyst comprising at least one porous support, at least some platinum, and at least a second group VIII metal different from platinum and iridium, said catalyst having been prepared by way of a method comprising, at least:
 a) impregnation of the support with at least one solution containing a platinum precursor,
 b) activation in a neutral or oxidising atmosphere, at a temperature of between 120 and 800° C.,
 c) activation in a reducing medium, at a temperature of between 0 and 800° C.,
 d1) impregnation with an aqueous solution and d2) treatment with at least one hydrogen donor compound, at a temperature of less than 200° C., the order in which steps d1) and d2) are carried out not mattering, provided that said steps are carried out after said step c) and before step e) which follows,
 e) impregnation of the support, having already been impregnated with platinum, by means of at least one solution containing a precursor of a second group VIII metal other than platinum and iridium,
 f) activation in a neutral, reducing or oxidising atmosphere, at a temperature of between 100 and 800° C.

The porous support used in the catalyst according to the invention is selected from titanium oxides, zirconium oxides, aluminas, silica-aluminas, chlorinated aluminas, aluminas promoted by fluorine, silicon, zirconium or titanium. The aluminas can be selected from ro alumina, gamma alumina, eta alumina, delta alumina, theta alumina, kappa alumina, alpha alumina, and mixtures thereof. The porous support is preferably selected from aluminas and chlorinated aluminas, and, very preferably, said porous support is a chlorinated alumina.

A chlorinated alumina is generally prepared by impregnating an alumina with hydrochloric acid. The impregnation can be carried out by various techniques known to the skilled person, such as "dry" impregnation or impregnation with an excess of solution. In "dry" impregnation, a hydrochloric acid solution is placed in contact with the alumina, e.g. by sprinkling the solution on alumina balls or extrudates. The volume of hydrochloric solution is selected to be equal to the pore volume of the alumina, so that the impregnated alumina keeps a virtually dry appearance, even at the end of impregnation. The concentration of hydrochloric acid in the solution is selected in consideration of the fact that all the chlorine is fixed by the alumina. With impregnation with an excess of solution, a hydrochloric acid solution is placed in contact with the alumina, the volume of solution being clearly greater than the pore volume of the alumina. An exchange takes place between the chlorine ions in solution and the surface of the alumina. The quantity of chlorine which is fixed by the alumina is a function of the exchange conditions: concentration of chlorine in the solution, temperature, duration of exchange. The preferred concentration of chlorine in alumina depends on the type of alumina and on its specific surface area. A mass concentration of between 0.5 and 2% by weight of chlorine in alumina is generally selected for chlorinating a gamma alumina with a specific surface area of between 150 and 300 $m^2/g$.

According to the invention, said porous support is advantageously in the form of balls, extrudates, pellets or powder. Very advantageously, said support is in the form of balls or extrudates. The pore volume of the support is between 0.1 and 1.5 $cm^3/g$, preferably between 0.4 and 0.8 $cm^3/g$. That pore volume is a result of the presence, mainly of mesopores with a pore diameter of between 3 and 20 nm. Said porous support has a specific surface area which is advantageously between 150 and 300 $m^2/g$.

The catalyst according to the invention contains a second group VIII metal from the Periodic Classification of Elements, which is different from platinum and iridium. It is selected from ruthenium, rhodium, iron, cobalt, and nickel. Said second group VIII metal is preferably rhodium.

The catalyst according to the invention also advantageously contains chlorine.

The catalyst according to the invention contains, more particularly:
 at least some platinum which is present in said catalyst, the content by weight thereof representing between 0.1 and 4% by weight, preferably between 0.2 and 2% by weight, and, very preferably, between 0.3 and 1.5% by weight of the catalyst,
 at least one second group VIII metal from the Periodic Classification of Elements, which is different from platinum and iridium, and which is selected from rhodium, ruthenium, iron, cobalt and nickel, preferably rhodium, present in said catalyst in a content by weight which represents between 0.05 and 3% by weight, preferably between 0.1 and 1% by weight, and, very preferably, between 0.2 and 0.6% by weight of the catalyst.

possibly chlorine present in said catalyst in a content by weight which represents between 0.1 and 3% by weight, preferably between 0.2 and 2% by weight, and, very preferably, between 0.3 and 1.5% by weight of the catalyst, at least one porous support which makes up the complement to 100% by weight in the catalyst.

Step a) of the process for preparation of the catalyst according to the invention consists in placing at least one platinum precursor in solution in an organic or inorganic solvent. The impregnation can be carried out with a volume of solution of between one tenth of the pore volume of the support and one hundred times the pore volume of said support. The skilled person will adapt the process in accordance with the morphology of said porous support, depending upon whether it is in the form of balls, powder, extrudates, or pellets. To carry out said step a), the platinum precursor is selected, in particular, from chloroplatinic acid, hydroxyplatinic acid, dinitroso-diammino platinum, tetramine platinum nitrate or chloride, chloroplatinic acid being preferable. The concentration of the platinum precursor in the solution is selected such that at the end of the process for preparation of the catalyst according to the invention the concentration of platinum in said catalyst, expressed by weight in relation to said catalyst, is between 0.1 and 4% by weight, preferably between 0.2 and 2% by weight, and, very preferably, between 0.3 and 1.5% by weight. The solution containing the platinum precursor can, if necessary, contain ions of hydrogen, ammonium, chlorides and nitrates for modifying the acid-base properties of the medium and/or for modifying the number of exchange sites of the porous support.

The temperature for impregnation with the platinum precursor is generally between 0 and 100° C., preferably between 10 and 50° C. The duration of the impregnation is generally between 1 minute and 10 hours, preferably between 2 minutes and 4 hours. In accordance with step b) of the process for preparing the catalyst according to the invention, the porous support, impregnated with platinum, is heat-activated at a temperature of between 120 and 800° C., preferably of between 300 and 600° C. The treatment atmosphere is oxidising or neutral. It can, for example, be constituted by nitrogen, argon, air, oxygen, gases from the combustion of mixtures of air and hydrocarbons in a concentration of less than or equal to 1, and mixtures thereof, preferably being air. The treatment duration is generally between 30 minutes and 30 hours, preferably between 1 and 6 hours.

The support which has been treated in this way in accordance with step b) is subjected to a treatment in a reducing medium, at a temperature of between 0 and 800° C., preferably of between 100 and 550° C., in accordance with step c) of the process for preparation of the catalyst according to the invention. Said reducing medium contains pure compounds or mixtures of compounds, such as, for example, hydrogen, carbon monoxide, saturated or unsaturated aliphatic or aromatic hydrocarbons, such as methane, ethane, propane, butane, ethylene, propylene, acetylene, benzene, or toluene, carboxylic acids such as formic acid or acetic acid, aldehydes such as formaldehyde or acetaldehyde, alcohols such as methanol, ethanol or propanol, polyols such as ethylene glycol or propylene glycol, amines such as methylamine or ethylamine, isocyanic acid, hydroxylamine, hydrazine, urea, combustion gases from mixes of air and hydrocarbons with a concentration of above 1, and mixtures thereof. Preferably, the reducing medium contains hydrogen. Very preferably, said step c) is carried out in the presence of hydrogen, at a temperature of between 100 and 550° C. It is advantageous to mix said reducing compounds with an inert compound, such as, for example, nitrogen or argon, which does not alter the reducing character of the afore-mentioned reducing compounds. To carry out step c), the solid which results from said step b) is generally introduced into a glass assembly comprising a tube which slides inside a vertical furnace. The tube is equipped with a frit which supports said solid comprising platinum on the support. At the bottom of the tube there is a system for feeding the various gases and for draining off the liquids. At the top of the tube, there is a glass ampoule equipped with a lower tap for connection to the tube and with 3 upper taps for gases to escape and for reagents to be introduced. Said solid which results from said step c) is placed in the tube.

Step c) of the process for preparation of the catalyst according to the invention is followed either by a step d1) which consists in impregnating said support resulting from said step c) with an aqueous solution, or by a step d2) which consists in treating said support resulting from said step c) with at least one hydrogen donor compound at a temperature of between 0 and 200° C., preferably of between 10 and 50° C. The order in which steps d1) and d2) are carried out does not matter, provided that said steps are carried out after said step c) and before step e) described hereinafter in the description: either, step d1) precedes step d2), or step d2) precedes step d1). According to step d1), impregnation of the support which results from step c), or from step d2), takes place through the use of an, aqueous solution at a temperature of between 10° C. and 100° C., preferably of between 10 and 40° C. Step d1) lasts between 15 and 30 minutes. The volume of said aqueous solution which is used for the impregnation in accordance with step d1) is greater than, or equal to, the pore volume of the support plus the intergranular volume, in such a way that the catalyst bed is covered with solution. The volume of solution is generally between 0.5 and 50 ml per g of solid, preferably between 1 and 20 ml per g of solid. The aqueous solution can be constituted solely by water, or comprise water and a competitor agent, such as chlorine, the competitor agent, preferably chlorine, having a concentration of between 0.01 and 1% in said aqueous solution. The excess aqueous solution is removed by flowing out, the excess solution being collected in a receptacle. When step d1) precedes step d2), the excess of said aqueous solution can be removed either before, or immediately after, step d2). In accordance with step d2), said hydrogen donor compound is advantageously selected from hydrogen, ammonia, saturated or unsaturated aliphatic hydrocarbons, and aromatic hydrocarbons, preferably hydrogen. Said step d2) is preferably carried out at a temperature of between 10 and 50° C. It lasts between 5 and 60 minutes, and, preferably, between 10 and 30 minutes. When step d1) precedes said step d2), the support which results from step c) is brought to ambient temperature, and is advantageously subjected to scavenging by means of a neutral gas, e.g. nitrogen, prior to step d1) itself being carried out. According to step e) of the process for preparation of the catalyst according to the invention, said porous support, which has already been impregnated with platinum during the course of step a), is impregnated with at least one solution which contains at least one precursor of a second group VIII metal other than platinum and iridium. The volume of solution containing at least said precursor of said second metal is advantageously between one tenth and one hundred times the pore volume of said support, preferably being between five and ten times the pore volume of said support. To carry out step e), the precursor of the second group VIII metal is selected from compounds which are soluble in an inorganic or organic medium. In particular, the following can be mentioned: chlorides, chlorinated acids, non-chlorinated acids, nitrates, amined complexes, carboxylic acid salts. When said second group VIII metal is rhodium, the rhodium precursor is selected, in particular, from rhodium chloride, rhodium nitrate, pentamine chloro rhodium-chloride, rhodium acetylacetonate. The concentration of precursor in the second group VIII metal, preferably rhodium, in the solution is selected such that at the end of the process for preparation of the catalyst according to the invention the concentration of the second group VIII metal other than platinum and iridium, in particular the concentration of rhodium, in said catalyst, expressed by weight in relation to said catalyst, is between 0.05 and 3%, preferably between 0.1 and 1%, and, very preferably, between 0.2 and 0.6%. The solution containing the precursor of the second group VIII metal, preferably rhodium, can, if necessary, contain hydrogen ions, ammonium, chlorides, nitrates. The temperature at which the precursor is impregnated with the second group VIII metal, preferably rhodium, is generally between 0 and 100° C., preferably between 10 and 40° C. Impregnation generally lasts for between 1 minute and 10 hours, preferably for between 2 minutes and 4 hours.

Impregnation of the precursor of the second group VIII metal, preferably rhodium, takes place in a neutral, or oxidising, or, even, reducing atmosphere. Step e) is preferably carried out in a gaseous atmosphere deprived of hydrogen.

Preparation of the catalyst according to the invention ends with a step f) which consists in activating the porous support impregnated with platinum and said second group VIII metal, preferably rhodium, in a neutral, reducing, or oxidising atmosphere, at a temperature of between 100 and 800° C., preferably of between 300 and 600° C., possibly followed by activation in a reducing medium, at a temperature of between 0 and 800° C., preferably of between 100 and 500° C.

In order to increase the content of the second group VIII metal and to control its addition to the catalyst, step e) is advantageously followed immediately by a step e1) comprising, at least, scavenging of the catalyst resulting from said step e) in hydrogen, followed by renewed impregnation of said catalyst by means of a solution containing at least one precursor of said second group VIII metal, preferably rhodium. Step e1) is reproduced until the desired content of the second group VIII metal, preferably rhodium, is obtained in the catalyst according to the invention.

The present invention also relates to use of the catalyst according to the invention in a process for the selective opening of at least one naphthenic compound selected from methylcyclopentane, methylcyclohexane and a mixture thereof.

According to the invention, the process for selective opening of the methylcyclopentane and/or the methylcyclohexane according to the invention seeks to produce paraffins which are preferably single-branched. The selective opening of the methylcyclopentane and/or methylcyclohexane, which is carried out in accordance with the process of the invention, requires the cutting of a single carbon-carbon bond of methylcyclopentane and/or of methylcyclohexane. The selective opening of the methylcyclopentane results in 2-methylpentane, 3-methylpentane and/or n-hexane. The selective opening of the methylcyclohexane results in 2-methylhexane, 3-methylhexane and/or n-heptane. Undesirable secondary reactions associated with the dehydrogenation of methylcyclopentane and/or methylcyclohexane, with the isomerisation of the linear and single-branched paraffins produced, and also with the cracking of the methylcyclopentane and/or of the methylcyclohexane can be observed, and must be limited to the maximum extent in order to promote the main reaction, namely that of the selective opening of methylcyclopentane and/or methylcyclohexane.

The process for the selective opening of methylcyclopentane and/or methylcyclohexane according to the invention generally takes place under the following conditions: a temperature of between 200 and 500° C., preferably of between 250 and 400° C., a total pressure of between 2 and 5 MPa, preferably of between 2.5 and 4 MPa, a $H_2$/naphthenic compound(s) molar ratio of between 3 and 8, and a ppH (hourly mass flow rate of charge/mass of catalyst) of between 2 and 20 $h^{-1}$, preferably of between 2 and 10 $h^{-1}$.

The following examples illustrate the invention.

EXAMPLE 1 (INVENTION)

Preparation of a Catalyst Comprising Platinum and Rhodium a) Ten grams of a gamma alumina support with a specific surface are of 215 $m^2$/g and a pore volume of 0.6 $cm^3$/g and in the form of balls of 2 mm in diameter are impregnated, with agitation, in a beaker, with 15 $cm^3$ of a hydrochloric acid solution at the rate of 1 mole/liter. After 15 minutes, 50 $cm^3$ of a chloroplatinic acid solution containing 0.12 g of platinum is added with agitation. After one hour's contact with the solution containing the chloroplatinic acid, the beaker is placed in a sand bath at 60° C., and is kept under agitation until the solution has evaporated. The beaker is then placed in a furnace at 120° C. for 16 hours.

b) The alumina which has been impregnated with chloroplatinic acid is introduced into a tubular furnace and is subjected to a calcination treatment in air at a rate of 10 L/h with the temperature increasing from ambient temperature at 10° C./minute up to 450° C., followed by a 4 hour period of remaining constant at 450° C. A calcined solid results which comprises platinum on alumina.

c) Said calcined solid is introduced into a glass assembly comprising a tube which slides inside a vertical furnace. The tube is equipped with a frit which supports said solid. At the bottom of the tube there is a system for feeding the various gases and for discharging the liquids. At the top of the tube there is a glass ampoule equipped with a lower tap for connection to the tube and with 3 upper taps for gases to escape and for reagents to be introduced.

The calcined solid of platinum on alumina is placed in the tube and then reduced in hydrogen (10 L/h) whilst the temperature increases at a rate of 10° C./minute from ambient temperature to 500° C., followed by a one hour period of remaining constant at 500° C., followed by a return to ambient temperature.

d1) The solid is then scavenged with a nitrogen flow (10 L/h) for 15 minutes, and is then moistened with 15 $cm^3$ of pure deaerated water introduced from a glass ampoule. The excess aqueous solution is removed by discharge.

d2) The solid is then scavenged at ambient temperature by a hydrogen flow of 10 L/h for 15 minutes, and then by a nitrogen flow of 10 L/h for 15 minutes.

e) Two hundred ml of a rhodium nitrate solution containing 0.04 g rhodium is introduced into the ampoule, then purged in nitrogen for 10 minutes. The solution is then poured onto the solid comprising platinum on alumina. The solid-solution structure is agitated by a nitrogen counter-current (2 L/h) for 5 minutes. The flow rate of nitrogen is then increased at 10 L/h to ambient temperature, and the catalyst is dried under these conditions for 45 minutes.

f) The nitrogen flow is replaced by hydrogen (10 L/h), and the temperature is increased to 100° C. After 12 hours, the temperature of the catalyst is increased to 500° C. at a rate of 2° C./minute, and it is then kept at that value for one hour.

The catalyst C1 which has been thus prepared contains in addition to alumina 1.17% by weight of platinum, 0.39% by weight of rhodium, and 1.4% by weight of chlorine.

EXAMPLE 2 (COMPARATIVE)

Preparation of a Catalyst Comprising Platinum and Rhodium a) Ten grams of a gamma alumina support with a specific surface area of 215 m$^2$/g and a pore volume of 0.6 cm$^3$/g and in the form of balls with a diameter of 2 mm are impregnated, with agitation, in a beaker, with 15 cm$^3$ of a hydrochloric acid solution equal to 1 mol/l. After 15 minutes, 50 cm$^3$ of a chloroplatinic acid solution containing 0.12 g of platinum is added with agitation. After one hour of contact with the solution containing the chloroplatinic acid, the beaker is placed on a sand bath at 60° C., and is kept under agitation conditions until the solution has evaporated. The beaker is then placed in a stove at 120° C. for 16 hours.

b) The alumina which has been impregnated with the chloroplatinic acid is introduced into a tubular furnace, and is subjected to a calcination treatment, in air, at a flow rate of 10 L/h, the temperature increasing from ambient temperature, at a rate of 10° C./minute, up to 450° C., followed by a 4 hour period of remaining constant at 450° C. A calcined solid results which comprises platinum on alumina.

c) Said calcined solid is introduced into a glass assembly comprising a tube which slides inside a vertical furnace. The tube is equipped with a frit which supports said solid. At the base of the tube there is a system for feeding the various gases and for discharging the liquids. At the top of the tube there is a glass ampoule which is equipped with a lower tap for connection to the tube, and with 3 upper taps for the gases to escape and for reagents to be introduced.

The solid comprising the platinum on alumina is placed inside the tube, and is then reduced in the presence of hydrogen (10 L/h) whilst the temperature rises at a rate of 10° C./minute from ambient temperature up to 500° C., followed by a one hour period of remaining constant at 500° C., followed by a return to ambient temperature.

d2) Said solid is then scavenged at ambient temperature by means of a hydrogen flow at a rate of 10 L/h for 15 minutes, and then by means of a nitrogen flow at a rate of 10 L/h for 15 minutes.

e) Two hundred ml of a rhodium nitrate solution containing 0.04 g rhodium is introduced into the ampoule, and is then purged in the presence of nitrogen for 10 minutes. The solution is then poured onto said solid comprising platinum on alumina. The solid-solution structure is agitated for 5 minutes by a nitrogen countercurrent (2 L/h). The flow rate of the nitrogen is then increased at up to 10 L/h to ambient temperature, and the catalyst is dried under these conditions for 45 minutes.

f) The nitrogen flow is replaced by hydrogen (10 L/h), and the temperature is increased to 100° C. After 12 hours, the temperature of the catalyst is increased to 500° C. at a rate of 2° C./minutes, and is then kept at that value for one hour.

The catalyst C2 which has thus been prepared also contains alumina, 1.17% by weight of platinum, 0.39% by weight of rhodium and 1.4% by weight of chlorine.

EXAMPLE 3 (COMPARATIVE)

Preparation of an Iridium-Based Catalyst a) Ten grams of a gamma alumina support with a surface area of 215 m$^2$/g and a pore volume of 0.6 cm$^3$/g and in the form of 2 mm diameter balls is impregnated, with agitation, in a beaker, with 15 cm$^3$ of a hydrochloric acid solution with a pH of 1. After 15 minutes, 50 cm$^3$ of a chloroiridic acid solution containing 0.16 g iridium is added, with agitation. After one hour of contact with the solution which contains the chloroiridic acid, the beaker is placed on a sand bath at 60° C., and is kept under agitation conditions until the solution has evaporated. The beaker is then placed in a furnace at 120° C. for 16 hours.

b) The alumina which has been impregnated with chloroiridic acid is introduced into a tubular furnace, and is subjected to a calcination treatment in air, at a rate of 10 L/h, and each hour, the temperature rising from ambient temperature at a rate of 10° C./minute up to 300° C., followed by a 4 hour period of remaining constant at 300° C., followed by cooling to ambient temperature. An iridium catalyst on calcined alumina results.

c) The calcined catalyst is then reduced in the presence of hydrogen (10 L/h), the temperature rising at a rate of 2° C./minute up to 500° C., followed by a 4 hour period of remaining constant at 500° C.

The catalyst C3 which has thus been prepared also contains alumina, 1.56% by weight of iridium, and 1.47% by weight of chlorine.

EXAMPLE 4

Use of the catalysts C1, C2 and C3 in the opening of methylcyclohexane and/or of methylcyclopentane.

The catalysts from Examples 1 to 3 (C1, C2 and C3) are tested in succession for the opening of the ring of methylcyclohexane, of methylcyclopentane, and of the methylcyclohexane-methylcyclopentane mixture in an installation comprising:

- a circuit for the supply of hydrogen to permit regulation of flow rate and pressure by way of a Brooks 5866 flow meter,
- a circuit for the supply of liquid charge, at a flow rate controlled by a piston pump,
- a metal reactor placed in a furnace,
- a pressure regulator,
- a gas-liquid separator placed on the circuit for effluents from the reactor,
- a Varian 3400 chromatograph equipped with an alumina PLOT column for separating the products for the opening of the ring, cracking products, isomerisation products and dehydrogenation products.

Before each of the tests, each of the catalysts C1 to C3 is crushed to a grain size of between 200 and 400 microns. Each of the catalysts C1 to C3 is then loaded (250 mg) into the reactor between two beds of carborundum for the purpose of improving the hydrodynamics of the catalytic bed.

In a first step, each of the catalysts C1 to C3 is reduced for one hour at 500° C. in the presence of hydrogen (40 bars, 3.6 L/h). The temperature is lowered to 200° C., and the liquid charge (methylcyclohexane, methylcyclopentane or a 50-50 mix by mass of methylcyclohexane-methylcyclopentane) is injected at a PPH of 2.5 (2.5 g/g of catalyst/hour) at a total pressure of 3 MPa. The molar flow rate of $H_2$/hydrocarbons is set at 5.

Chromatographic analysis of the reaction products shows that a transformation stage is reached at the end of 2 hours. The temperature is then increased by 25° C. in 2 hours, and then a 2 hour constant period is established. This temperature increase cycle followed by a constant period is followed for every 25° C., up to 400° C.

The table hereinafter compares the maximum yields in the opening of the ring for tests carried out with pure methylcyclohexane (MCH), pure methylcyclopentane (MCP) and a mixture of methylcyclohexane-methylcyclopentane (MCH-MCP):

|  | MCH | MCP | MCH-MCP |
|---|---|---|---|
| catalyst C1 | 55% | 41 | 44 |
| catalyst C2 | 53% | 39 | 42 |
| catalyst C3 | 42% | 37 | 39 |

The catalyst C1 according to the invention gives a maximum yield of ring-opening products which is markedly higher than catalyst 3, and still substantially higher than catalyst 2.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 06/09.766, filed Nov. 7, 2006, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A catalyst comprising at least one porous support, platinum, and rhodium, said catalyst having been prepared by a method comprising:
   a) impregnation of the support with at least one solution containing a platinum precursor,
   b) activation of resultant impregnated support from step (a) in a neutral or oxidising atmosphere, at a temperature of between 120 and 800° C.,
   c) further activation in a reducing medium, at a temperature of between 0 and 800° C.,
   d1) impregnation of catalyst from step (c) with an aqueous solution and d2) treatment with at least one hydrogen donor compound at a temperature of less than 200° C., the order in which steps d1) and d2) are carried out being optional, provided that said steps are carried out after said step c) and before step e) which follows,
   e) impregnation of the support, impregnated with platinum, with at least one solution containing a rhodium precursor, and
   f) activation of catalyst from step e) in a neutral, reducing or oxidising atmosphere, at a temperature of between 100 and 800° C.

2. A catalyst according to claim 1, wherein said porous support is selected from aluminas and chlorinated aluminas.

3. A catalyst according to claim 1, comprising between 0.1 and 3% by weight of chlorine.

4. A catalyst according to claim 1, wherein said platinum precursor in said step a) is chloroplatinic acid.

5. A catalyst according to claim 1, wherein said step b) is carried out at a temperature of between 300 and 600° C.

6. A catalyst according to claim 1, wherein said step c) is carried out in the presence of hydrogen, at a temperature of between 100 and 550° C.

7. A catalyst according to claim 1, wherein said aqueous solution which is used in accordance with step d1) is either constituted by water alone, or comprises water and a competitor agent.

8. A catalyst according to claim 1, wherein said hydrogen donor compound which is used in step d2) is hydrogen.

9. A catalyst according to claim 1, wherein said precursor of said second group VIII metal, which is present in the solution used in said step e), is a rhodium precursor.

10. A catalyst according to claim 1, wherein said activation in a neutral or oxidising atmosphere in accordance with step f) is followed by activation in a reducing medium at a temperature of between 0 and 800° C.

11. A catalyst according to claim 1, further comprising, scavenging the catalyst resulting from said step e), in hydrogen, followed by renewed impregnation of resultant scavenged catalyst with a solution containing at least a precursor of rhodium.

12. A process for the selective opening of at least one naphthenic compound selected from methylcyclopentane, methylcyclohexane, and a mixture thereof carried out in the presence of a catalyst according to claim 1, said process being carried out at a temperature of between 200 and 500° C., a total pressure of between 2 and 5 MPa, a $H_2$/naphthenic compound(s) molar ratio of between 3 and 8, and a ppH (hourly mass flow rate of charge/mass of catalyst) of between 2 and 20 $h^{-1}$.

13. A catalyst according to claim 1, comprising between 0.1 and 4% by weight of platinum and between 0.05 and 3% by weight of rhodium.

14. A catalyst according to claim 13, wherein said porous support is selected from aluminas and chlorinated aluminas.

15. A catalyst according to claim 14, comprising chlorine.

16. A catalyst according to claim 15, comprising between 0.3 and 1.5% by weight of platinum and between 0.2 and 0.6% by weight of rhodium.

17. A method for preparing a catalyst comprising a porous support, platinum and rhodium, said method comprising
   a) impregnation of the support with at least one solution containing a platinum precursor,
   b) activation of resultant catalyst from step a) in a neutral or oxidising atmosphere, at a temperature of between 120 and 800° C.,
   c) further activation in a reducing medium, at a temperature of between 0 and 800° C.,
   d1) impregnation with an aqueous solution and d2) treatment with at least one hydrogen donor compound at a temperature of less than 200° C., the order in which steps d1) and d2) are carried out being optional, provided that said steps are carried out after said step c) and before step e) which follows, e) impregnation of the support impregnated with platinum, with at least one solution containing a rhodium precursor, and f) activation of resultant catalyst from step (e) in a neutral, reducing or oxidising atmosphere, at a temperature of between 100 and 800° C.

18. A method according to claim 17, wherein said aqueous solution consists of water or water containing between 0.01 and 1% by weight of chlorine, and the support is a chlorinated alumina.

19. A process for the selective opening of at least one naphthenic compound selected from methylcyclopentane, methylcyclohexane, and a mixture thereof carried out in the presence of a catalyst according to claim 13, said process being carried out at a temperature of between 200 and 500° C., a total pressure of between 2 and 5 MPa, a $H_2$/naphthenic compound(s) molar ratio of between 3 and 8, and a ppH (hourly mass flow rate of charge / mass of catalyst) of between 2 and 20 $h^{-1}$.

20. A process for the selective opening of at least one naphthenic compound selected from methylcyclopentane, methylcyclohexane, and a mixture thereof carried out in the presence of a catalyst according to claim 15, said process being carried out at a temperature of between 200 and 500° C., a total pressure of between 2 and 5 MPa, a $H_2$/naphthenic compound(s) molar ratio of between 3 and 8, and a ppH (hourly mass flow rate of charge/mass of catalyst) of between 2 and 20 $h^{-1}$.

21. A process for the selective opening of at least one naphthenic compound selected from methylcyclopentane, methylcyclohexane, and a mixture thereof carried out in the presence of a catalyst according to claim 16, said process being carried out at a temperature of between 200 and 500° C., a total pressure of between 2 and 5 MPa, a $H_2$/naphthenic compound(s) molar ratio of between 3 and 8, and a ppH (hourly mass flow rate of charge/mass of catalyst) of between 2 and 20 $h^{-1}$.

22. A catalyst according to claim 1, the resultant catalyst providing greater naphthenic ring opening activity than a similar catalyst prepared without a step of impregnation with an aqueous solution according to steps (d1) and without said treatment according to step (d2).

* * * * *